United States Patent [19]

Walele et al.

[11] Patent Number: 4,791,097
[45] Date of Patent: Dec. 13, 1988

[54] BENZOIC ACID ESTERS AND THEIR USE

[75] Inventors: Ismail Walele, Saddle Brook; Herman Brown, Teaneck; Michael Esposito, Randolph, all of N.J.

[73] Assignee: Finetex, Inc., Elmwood Park, N.J.

[21] Appl. No.: 23,767

[22] Filed: Mar. 9, 1987

[51] Int. Cl.$^4$ .................... C07C 9/76; C09B 3/22
[52] U.S. Cl. .................... 560/112; 252/358; 560/103
[58] Field of Search .................... 560/103, 112; 252/358

[56] References Cited

U.S. PATENT DOCUMENTS

| | | | |
|---|---|---|---|
| 2,840,594 | 1/1958 | Coates | 560/112 |
| 4,323,693 | 4/1982 | Scala | 560/103 |
| 4,323,694 | 4/1982 | Scala | 560/103 |
| 4,365,084 | 12/1982 | Young | 560/103 |
| 4,431,837 | 2/1984 | Geria | 560/112 |
| 4,559,226 | 12/1985 | Fogil | 560/103 |

*Primary Examiner*—Paul J. Killos
*Attorney, Agent, or Firm*—Weingram & Zall

[57] ABSTRACT

A method is provided for modifying foam in an aqueous surfactant composition. The method comprises admixing with the aqueous surfactant composition a foam modifying amount of a composition of the formula:

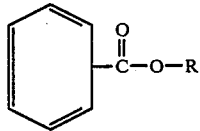

wherein R is:
(a) a branched or linear alkyl of 20 to 28 carbon atoms; or (b)

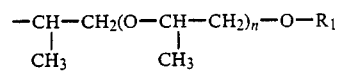

wherein n is 9–16 and $R_1$ is a branched or linear alkyl of 3 to 22 carbon atoms.

Certain of these benzoate esters are novel, in particular:

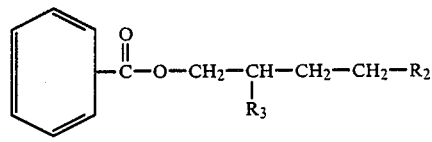

wherein $R_2$ and $R_3$ are each, independently, an alkyl of 4 to 16 carbon atoms, and the total number of carbon atoms in $R_2$ and $R_3$ is at least 12 carbon atoms. Preferably, $R_2$ and $R_3$ are each $C_8H_{17}$, i.e. octyldodecyl benzoate ester.

Additional novel benzoate esters used as foam enhancers have the formula:

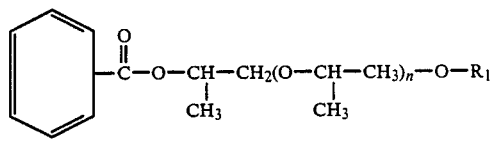

wherein n is 12 to 16 and $R_1$ is a branched or linear alkyl of 3 to 22 carbon atoms. Particularly preferred esters are when n is 14, $R_1$ is $C_{18}H_{37}$ and $R_1$ is $C_4H_9$. Also, additionally, preferred esters are where n is 9 and $R_1$ is $C_{16}H_{33}$.

10 Claims, No Drawings

BENZOIC ACID ESTERS AND THEIR USE

BACKGROUND OF THE INVENTION

1. Field of the Invention

This invention relates generally to improved ester compositions, and more particularly to certain benzoic acid esters of alcohols which are useful as foam modifiers as well as diluents, solvents, plasticizers, liquid carriers, emollients, conditioners.

2. Description of the Prior Art

There are numerous references which describe the production and use of benzoic acid esters. None of these references teach or suggest the specific novel benzoate esters of this invention or the use of these and other benzoate esters as foam modifiers in detergent compositions. More specifically:

U.S. Pat. No. 2,088,085 to Gross describes a composition added to solutions to produce a stable foam, especially for fire extinguishing purposes. The compound is an ether which the formula $R_1$—(O—$CH_2$—$CH_2$)$_n$—O—$R_2$ where $R_1$ is a hydrogen atom or an alkyl radical and $R_2$ may be an alkyaryl or aryl radical, n may be a whole number and the total number of carbon atoms is at least three.

U.S. Pat. No. 3,510,500 to Walsh describes a process for preparing an ester by reacting a monobasic organic acid, which may be a benzoic acid, with an organic halide. This reaction requires the removal of hazardous hydrogen halide gas as a byproduct.

U.S. Pat. No. 3,714,228 to Massie describes the production of an ester by reacting a carboxylic acid with an alcohol. An example of a carboxylic acid mentioned therein is benzoic acid and an example of an alcohol is eicosene alcohols ($C_{20}$ alcohols).

U.S. Pat. No. 3,799,969 to Hoppe describes the production of o-aminobenzoic acid-2-hexyldecyl-(1)-ester by the reaction of o-aminobenzoic acid and 2-hexyldecanol.

French Pat. No. 2,151,503 to Beiersdorf Ag. describes $H_2NC_6H_4CO_2CH_2CHRR_1$ as an intermediate, where R is H, C2-12 alkyl and $R_1$ is OBu, C4-14 alkyl.

European patent application No. 0 037 542 (corresponding to U.S. Pat. No. 4,339,342 to Hempel) describes the use of 2-octyldodecanol or a mixture of $C_{22-30}$ Guerbet alcohols and hydrophobic, colloidal silicic acid reacted to prepare an anti-foaming agent. This foam inhibition "is surprising in view of known foaming bath additives, such as, for example, those disclosed in German published application (DOS) No. 19 48 500, which contain from 5 to 50 percent of the Guerbet alcohol 2-octyldodecanol" (U.S. Pat. No. 4,339,342, Col. 2 lines 50-58). Although octyldodecanol is cited as a known "foaming bath additive", our work shows that benzoate esters from octyldodecanol are superior foam stabilizers/enhancers/modifiers when compared to octyldodecanol. This is unexpected in that one skilled in the art would assume that the ester would be a foam suppressor when compared to the reactant alcohol. Further, Hempel only teaches the use of octyldodecanol as a carrier or vehicle for foam inhibiting formulations and not as a reactant. Applicants herein only use octyldodecanol as a reactant.

The assignee herein, Finetex Incorporated, has published and patented inventions related to this art, in particular:

Cosmetics and Toiletries, "A new cosmetic fluid emollient for use in antiperspirants", 1980, 95(7), 51-4 by H. Brown describes the use of a $C_{12-15}$ benzoate ester fluid emollients (FINSOLV TN) in antiperspirant preparations.

U.S. Pat. No. 4,278,655 to Elmi describes the use of benzoic acid esters of a mixture of linear primary alcohols in the $C_9$ to $C_{15}$ carbon chain length range in antiperspirant compositions.

U.S. Pat. No. 4,275,222 to Scala, Jr., describes the benzoic acid esters of a mixture of C12, C13, C14 and C15 linear primary alcohols. The compositions described therein are said to have anti-foaming properties, i.e. they prevent foam from forming initially, and are used in hand cleaners, dispersable bath oils, and floating bath oils.

U.S. Pat. No. 4,293,544 to Elmi describes the use of benzoic acid esters of a mixture of C12, C13, C14 and C15 linear primary alcohols in toiletries, cosmetics, topical pharmaceuticals and the like.

U.S. Pat. No. 4,322,545 to Scala, Jr. describes benzoic acid esters wherein the alcohol is from C12 to C15 primary alcohols. The compositions described therein are said to lack greasiness, oiliness, have a low cloud point and pour point, bland odor, ability to form gels with suspending agents and low toxicity.

U.S. Pat. No. 4,323,693 to Scala, Jr. describes a substantially pure benzoic acid ester of isostearyl ($C_{18}$) alcohol for use as a carrier or vehicle, emollient or solublizer for cosmetic and toiletry formulations.

U.S. Pat. No. 4,323,694 to Scala, Jr. describes benzoic acid esters of alcohols which are branched primary alcohols up to $C_{18}$ and branched or linear alcohols up to $C_{19}$. The esters are used in bubble bath oils and do not significantly alter the foaming properties of the detergents (Col. 14, lines 21-26). When used in a toilet soap bar, "the user should readily observe a richer and denser lather compared to what he or she was used to from regular soap".

OBJECTS AND SUMMARY OF THE INVENTION

It is an object of this invention to provide a method of modifying, while not suppressing, foam in an aqueous surfactant composition using certain specific types of benzoic acid esters.

It is a further object of this invention to provide novel benzoic acid esters which may serve as emollients, solubilizers and carriers (dilutents) and which may also modify the foam and foaming characteristics, without significantly suppressing the foam or foaming characteristics, of the unmodified aqueous surfactant composition.

A method is provided for modifying foam and foaming characteristics of an aqueous surfactant composition. The method comprises admixing with the aqueous surfactant composition a foam modifying amount of a composition of the formula:

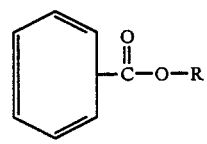

wherein R is:
(a) a branched alkyl of 20 to 28 carbon atoms; or
(b)

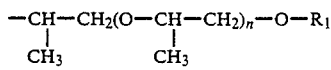

wherein n is 9–16 and $R_1$ is a branched or linear alkyl of 3 to 22 carbon atoms.

Certain of these benzoate esters are novel, in particular:

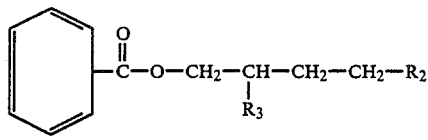

wherein $R_2$ and $R_3$ are each, independently, an alkyl of 4 to 16 carbon atoms, and the total number of carbon atoms in $R_2$ and $R_3$ is at least 12 carbon atoms.

Preferably, $R_2$ and $R_3$ are each $C_8H_{17}$, i.e. octyldodecyl benzoate ester.

Additional novel benzoate esters used as foam modifiers have the formula:

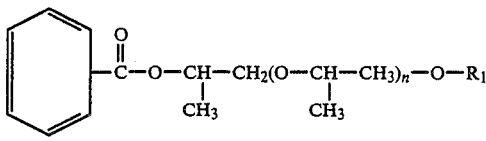

wherein n is 1 to 50 and $R_1$ is a branched or linear alkyl of 3 to 22 carbon atoms. Particularly preferred esters are when n is 14, $R_1$ is $C_{18}H_{37}$ and $R_1$ is $C_4H_9$. Additionally preferred esters are when n is 9 and $R_1$ is $C_{16}H_{33}$.

DETAILED DESCRIPTION OF THE INVENTION

The benzoic acid esters of this invention are produced by reacting benzoic acid with an alcohol. Preferably, stannous oxalate is used as a catalyst. It is contemplated, however, that any method of producing such benzoic acid esters can be utilized as long as such method does not interfere with their intended use. In particular, the process for producing the esters should permit them to be purified to a substantially pure condition. By the use of the term "substantially pure", it is meant that the compositions do not contain impurities which would interfere with their intended use, e.g. as foam modifiers in aqueous surfactant compositions.

The alcohol precursors used in preparing the benzoic acid esters are selected from the group consisting of:
(a) branched or linear alkanols of 20 to 28 carbon atoms; or
(b)

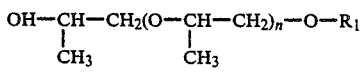

wherein n is 1 to 50 and $R_1$ is a branched or linear alkyl of 3 to 22 carbon atoms.

Particularly preferred alcohols are octyldodecanol, propoxylated stearyl alcohol i-e PPG-15 stearyl ether, arachidyl alcohol, behenyl alcohol, and alkanols of 20 to 28 carbon atoms in length, as exemplified by EPAL 20+ alcohol from Ethyl Corporation. The following is a list of alcohols which may be reacted with benzoic acid to produce the novel esters of this invention and the esters used in this invention:

(a) branched or linear alkanols of 20 to 28 carbon atoms:
  octyldodecanol
arachidyl alcohol
  behenyl alcohol
  $C_{20}+$ linear alcohols (Epal 20+)
(b)

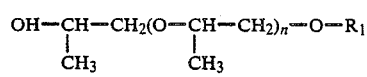

wherein n is 1 to 50 and $R_1$ is a branched or linear alkyl of 3 to 22 carbon atoms:
  Procetyl-10 (PPG-10 Cetyl Ether) from Croda Inc.
  Arlamol E (PPG-15 Stearyl Ether) from I.C.I.
  Generally propoxylated alkanols, linear or branched.

The aforedescribed alcohols are well known and commercially available.

The compositions of this invention are useful as foam modifiers for aqueous surfactant compositions. Aqueous surfactant compositions which can utilize such foam modifiers are:
  hand cleaners
  bath compositions
  facial cleansers
  cleansing creams
  hard surface cleaners
  shampoos
  'mousse' products
  shaving creams
  pet cleaners
  concrete air-entrainment products
  ore beneficiation products The foregoing list is only exemplary of the type of compositions in which the benzoic acid esters may be used and, as such, is not to be considered limiting.

The amount of ester used in the aqueous surfactant composition is dependent on the type of composition desired, the type and quantity of other ingredients used, e.g. cosmetic ingredients, and the amount and type of functional additives that are utilized. Typically, the amount ranges from about 0.5% to about 50% by weight of the aqueous surfactant composition. Preferably, from about 0.5% to about 5.0% of benzoic acid esters of this invention are used.

The afore-described benzoic acid esters have unique properties. In particular, they have foam modifying properties. By "foam modification" herein it is meant that the benzoic acid esters confer any or all of the following properties upon a surfactant composition:
  Flash foam increase
  Foam volume increase
  Foam viscosity increase or decrease
  Foam cell size increase or decrease.

While the particular foam modification is dependent upon the benzoic acid ester and surfactant of choice, no surfactant investigated has been observed to suffer a suppression of foam volume due to the presence of any of the benzoic acid esters investigated herein, i.e. none of the benzoic acid esters investigated were defoamers. Additionally, they have other properties which make them suitable for use as emollient carriers in cosmetic formulations, and for use as solvents and emollient carriers in general cleaning compositions. Further, they possess other unusual physico-chemical properties, in particular high spreading coefficients, which can make them beneficial and unique components of sophisticated delivery systems—such as in hand, face, and body creams and lotions.

The afore-described benzoic acid esters have the following properties:

1. Lack of greasiness, pleasant skin feel.
2. Lack of oiliness while imparting good lubrication.
3. Low cloud points and pour points.
4. Low toxicity.
5. Ease of emulsification.
6. Unusually high spreading coefficient.
7. Acid, alkaline stability.
8. Solvents for many common skin and hair care additives, including, sunscreens and over-the-counter therapy 'actives'.

The following are non-limiting examples of the compositions of this invention and the uses of these compositions in hair and skin care compositions wherein foam modification and properties related to application and delivery are useful.

| Skin Lotion (Sunscreen) | Wt % | Shampoo | Wt % | "Creamy" Soap Bar | Wt % |
|---|---|---|---|---|---|
| Water | 82.0 | Triethanol-amine Lauryl Sulfate | 12.0 | "Soap Chips"* | 98.0 |
| Glycerin | 3.0 | Lauramide DEA | 3.0 | Stearoxy PPG-15-Benzoate | 2.0 |
| Cetyl Alcohol | 2.0 | Octyldodecyl Benzoate | 5.0 | Color, fragrance | q.s |
| Stearoxy PPG-15-Benzoate | 5.0 | Ethylene Glycol Monostearate | 1.0 | | |
| Tween 80 | 4.0 | Water | 79.0 | | |
| Ethylene Glycol Monostearate | 1.0 | Color, fragrance | q.s | | |
| Escalol 507 | 3.0 | | | | |

*@ approx 10% water.

EXAMPLE 1

Preparation of Octyldodecyl Benzoate

A mixture of 213 gms. (0.715 moles) of STANDAMUL G from Henkel Co. (Octyldodecanol) and 15 mgms. Sodium borohydride was stirred at room temperature 25° C. under nitrogen. The mixture was then heated and brought to 60° C. and held at 60° C. for ½ hour. To this mixture was added 86.40 gms. (0.68 moles) Benzoic Acid and 450 mgms. of stannous oxalate. The reaction mixture was then further heated to 255° C. During the heat-up cycle, distillate was collected, particularly when the reaction mixture reached a temperature of 170° C. and higher. The reaction was rapidly heated from 60° C. to 177° C. over 45 minutes, and then from 177° C. to 228° C. over the next 60 minutes while still collecting the distillate. Further heating was continued to bring the temperature to 255° C. over the next 30 minutes. The distillate collected contained 7.5 gms. of water and also contained some benzoic acid trapped during the collection of distillate. The reaction was then cooled. The yield at this stage was 265 gm. and acidity was at 9.5 mgms. The KOH/gm. hydroxyl value of this mixture was 19.29. 220 gms. of this ester was treated with 2.2 gms. sodium carbonate, 1.1 gm. sodium chloride, 2.0 gms. Hydrogen peroxide in 35 gms. deionized water. The mixture was stirred and heated to 85°–90° C., held at 85°–90° C. for 30 minutes and allowed to stand for separation of the ester and water phases. The ester phase was separated and further washed with deionized water until reaction of the water was neutral. The ester collected was 200 gms. and was hydrous. The product was vacuum stripped to remove the residual moisture, and then filtered using filter-aids. The final product was a clear liquid and had the following formula:

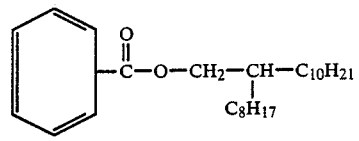

The following typical physical and chemical properties were observed:

| | |
|---|---|
| Specific Gravity @ 29° C.: | 0.90 |
| Surface Tension @ 25° C.: | 32.6 dynes/cm |
| Spreading Coefficient @ 25° C.: | 32.1 dynes/cm |
| Pour Point: | <−18° C. |
| Odor: | Bland |
| Toxicity: | Practically non-irritating (eyes), Primary Skin Irritation Score 0.7, LD$_5$>5.0 g/kg |
| Appearance: | Clear liquid |
| Viscosity @ 25° C. (Brookfield #1, 50 rpm): | 45 cps |

EXAMPLE 2

Preparation of Octyldodecyl Benzoate

A mixture of 710 gms. (2.38 moles) of Octyldodecanol (STANDAMUL G from Henkel Co.) and 50 mgms. Sodium borohydride was stirred into nitrogen. The mixture was heated to 60° C. and stirred for 30 minutes. 289 gms. (2.28 moles) of Benzoic Acid and 1.5 gms. of stannous oxalate was added. The reaction mixture was heated from 60° C. to 180° C. over one hour. The reaction was held at 180° C. for 30 minutes, distillate being collected. The mixture was further heated to 210°–220° C. over the next 30 minutes, and then held at 210°–220° C. for 30 minutes. The temperature was then raised to 250° C. and the reaction was then held at 250° C. for two hours. The reaction mixture was cooled under nitrogen to 50° C. The total distillate collected was 39.5 gms. This mixture had an acidity of 4.48 mgms. KOH/gm. The mixture was then treated with 16 gms. sodium carbonate, 5 gms. sodium chloride in 160 gms. deionized water containing 10 gms. Hydrogen peroxide and then heated to 80°–85° C. and held at 80°–85° C. for 30 minutes. The mixture was allowed to stand without stirring. The ester component was collected and washed with 160 gms. deionized water containing 5 gms. sodium chloride at 80°-85° C. and allowed to stand and separate. The ester collected weighed 870 gms. This was then vacuum stripped to remove the residual moisture and filtered using filter-aids (such as MAGNESOL from Reagent Chemical & Research, Inc. and HYFLOSUPERCELL CELATOM FW-60 from Eagle-Picher Industries). The dry yield was 850 gms. of a clear liquid.

EXAMPLE 3

Preparation of Stearoxy-PPG-15 -Benzoate

A mixture of 261 gms. (0.3 moles) of ARLAMOL E from I.C.I. Co. (Propoxylated Stearyl Alcohol, i.e. PPG-15-Stearyl Ether), 42 gms. (0.3 moles) of benzoic acid and 450 mgms. of stannous oxalate was stirred at 27° C. under nitrogen. The mixture was heated to 176° C. over one hour. The mixture was further heated to 230° C. over the next hour at which time distillate started coming off. Further heating was continued and the temperature raised to 250° C. over 30 minutes and held at 250° C. for one hour. The mixture was then heated to 265° C. and held at 265° C. for the next 40–45 minutes and allowed to cool. The reaction mass was then air-cooled to 165° C. Further cooling to 35° C. under nitrogen was accomplished by applying a cooling-water jacket. A clear light yellowish liquid was obtained. The yield for the reaction was 275 gms. Acidity was nearly zero and hydroxyl number was 22.26.

(a) 50 gms. of this ester was treated with 15 gms. deionized water and 0.5 gms. sodium carbonate at 50° C. The mixture was separated and the water layer drained off. The remaining composition was washed with 20 gms. deionized water at 60° C. The ester was then separated and collected and then vacuum stripped at 110° C.–130° C. to remove the residual moisture. The mixture was then cooled to 30° C. and showed slight haze. The liquid was heated with filteraids and filtered at 40° C., using Whatman Filter Paper #42. A crystal clear liquid of benzoate ester emollient was obtained. This clear liquid stayed a clear liquid at 7° C. when refrigerated and did not show any sedimentation or haze.

(b) 170 gms. of this ester was treated with 51 gms. deionized water containing 1.7 gms. sodium carbonate at 50° C. separated and further heated with fresh 68 gms. water at 60° C. The composition was then mixed and allowed to stand for separation. This separated ester was then vacuum stripped at 110°–130° C. and 10–15 mmHg, vacuum cooled to 25°–28° C. and filtered using 0.80 gms. of MAGNESOL and 1–60 gms. HYFLOSUPERCELL (from Johns-Manville Co.) as filter-aids. Filtration was done using Whatman Filter Paper #42. Final product was a clear liquid without odor.

The ester made had the following formula:

The following typical physical and chemical properties were observed:

| | |
|---|---|
| Specific Gravity @ 24° C.: | 0.98 |
| Surface Tension @ 25° C.: | 35.1 dynes/cm |
| Spreading Coefficient @ 25° C.: | 31.5 dynes/cm |
| Pour Point: | −12° C. |
| Odor: | Bland |
| Toxicity: Practically non-irritating (eyes), Primary Skin Irritation Score 0.8, | $LD_5 > 5.0$ g/kg |
| Appearance: | Clear liquid |
| Viscosity @ 25° C. (Brookfield #1, 50 rpm): | 158 cps |

EXAMPLE 4

Preparation of Stearoxy-PPG-15-Benzoate 870 gms. of ARLAMOL E (propoxylated stearyl ether i.e. PPG-15 Stearyl Ether) (I.C.I.) and 50 mgms. sodium borohydride was mixed and heated under nitrogen. The mixture was held at 60° C. for 30 minutes. 140 gms. of benzoic acid and 1–5 gms. stannous oxalate was added. The reaction mixture was then further heated to 200° C. over 30 minutes, and further raised to 240° C. over the next 30 minutes. The reaction was held at 240°–245° C. for 30 minutes and then raised to 265° C. and held at 265° C. for one hour. The distillate collected was 14.5 gms. against theoretical estimates of 14.5 gms. The reaction mixture was cooled to 35°–40° C. under nitrogen. The ester had the acidity of 5–84 mgms. KOH/gms. The reaction product was treated with 360 gms. deionized water containing 16 gms. sodium carbonate, 5 gms. sodium chloride at 80°–85° C. The ester was allowed to stand overnight. The top layer containing the benzoate ester was collected. It weighed 1037 gms. It was vacuum stripped at 115°–120° C. and 10–15 mm Hg vacuum. The liquid benzoate of this reaction weighed 850 gms. which was then treated with 2.25 gms. MAGNESOL and 4.25 gms. CELATOM FW-60 (Diatomaceous earth) at 50° C. and filtered at 50° C. The net yield of the liquid benzoate ester product was 835 gms.

EXAMPLE 5

Preparation of Arachidyl-Benzoate

A mixture of 104 gms. (0.348 moles) of arachidyl alcohol, 46 gms. (0.362 moles) of benzoic acid and 225 mgms. stannous oxalate was heated under nitrogen to 230° C. The reaction was held at 230° C. for two hours under nitrogen. The acidity was 10 mgms. KOH/gms. The mixture was then cooled to 100° C. During the reaction distillate was collected. The ester formed was solid at room temperature and showed solidification at 80° C. The ester was given a treatment at 85° C. with 50 gms. deionized water containing 2 gms. sodium carbonate, 2 gms. sodium chloride and 1 gm. hydrogen peroxide. The mixture was allowed to stand and separate. The top layer was washed with 50 gms. deionized water at 80°–85° C., separated and cooled. The top layer solidified and bottom layer was completely drained off. The

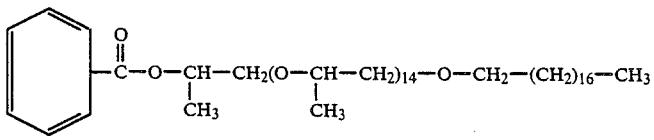

ester was then vacuum stripped at 100°-105° C. The ester so formed was a white solid benzoate.

The ester had the following formula:

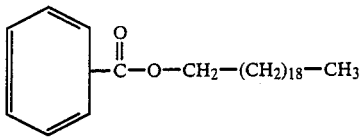

EXAMPLE 6

Preparation of Behenyl Benzoate

A mixture of 106.5 gms. (0.326 moles) of behenyl alcohol, 43.5 gms. (0.343 moles) of benzoic acid and 225 mgms. stannous oxalate was heated to 230° C. under nitrogen. The reaction was held at 230° C. for two hours, and the distillate collected. It was then cooled to 100° C. The acidity was 10.0 mg KOH/gm. The ester was then given a treatment for 30 minutes at 85° C. with 50 gms. deionized water, 2 gms. sodium carbonate, 2 gms. sodium chloride, and 1 gm. hydrogen peroxide. It was then allowed to stand and the lower aqueous layer drained off. The top layer was washed with 50 gms. water at 80°-85° C. and then separated. The solid was then vacuum stripped at 100°-105° C. to remove residual moisture. The final product was a solid benzoate ester having the following formula:

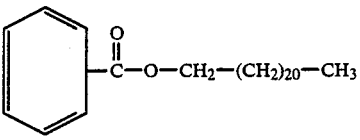

EXAMPLE 7

Preparation of Benzoate ester of a mixed 20+ Carbon Chain Distribution

A mixture of 155.04 gms. of Epal 20+ alcohol (Ethyl Corporation), 44.96 gms. of benzoic acid and 300 mgms. of stannous oxalate was heated to 228° C. under nitrogen. The distillate was collected during the reaction. The reaction mixture was cooled to 100° C. The acidity was 12 mgms. KOH/gm. 176 gms. of this mixed alcohol benzoate was treated with 65 gms. deionized water containing 2 gms. sodium carbonate, and 1 gm. hydrogen peroxide at 85° C. This mixture was very fluid and the bottom aqueous wash liquid was drained off. The top layer of the subject benzoate ester was further washed with 65 gms. deionized water at 75° C. The composition was allowed to stand and the ester layer removed. The net yield of this mixed alcohol benzoate ester was 120 gms. and the final product was a soft smooth paste at room temperature. The composition had the following formula:

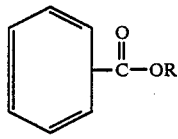

wherein R is a mixture of alky substituents from $C_{20}$ to $C_{28}$.

EXAMPLE 8

Preparation of Cetoxy-PPG-10-Benzoate 214 gms. Procetyl-10 (Cetoxyl-PPG-10 from Croda, Inc.) and 15 mgms. sodium borohydride were mixed and heated under nitrogen. 36 gms. of benzoic acid and 375 mgms. stannous oxalate were added. Reaction mixture was then heated to 250° C. over ½ hour and held @ 250° C. for the next 1 hour. Additional one hour of reaction time was @ 250° C. Reaction was then cooled to 50° C. under nitrogen. 235 gms. of this crude ester was obtained. This crude ester was treated at 80°-85° C. for ½ hour with 25 gms. water, 2 gms. sodium chloride, 5 gms. sodium carbonate and 5 gms. hydrogen peroxide. Allowed to stand for separation. The ester was separated and given a further wash with 50 gms. water and 1 gm. sodium chloride @ 65°-75° C. Allowed to separate and the ester layer was collected. The ester layer was further washed with 50 gms. water. Allowed to separate and the top hydrous ester layer was collected. The hydrous ester layer was vacuum stripped at 110°-120° C. @ 8-10 mm Hg. vacuum. The liquid benzoate ester of this reaction was then heated @ 35° C. with 0.5% Magnesol and 0.25% Celatom FW-60. The net yield of this benzoate ester was 180 gms.

EXAMPLE 9

Preparation of Butoxy-PPG-15-Benzoate 220 gms. Ucon LB-285 (PPG-15-Butyl ether from Union Carbide) and 15 mgms. sodium borohydride were mixed and heated under nitrogen. 30 gms. benzoic acid and 375 mgms. stannous oxalate were added. Reaction mixture was then heated to 250° C. and held @ 250° C. for 1½ hours. The reaction mixture was cooled to 50° C. and to this was added 1 gm. hydrogen peroxide and then heated to 80°-85° C. for ½ hour. 234 gms. of the crude ester was further treated with 20 gms. water, 2 gms. sodium carbonate and 1 gm. sodium chloride @ 80° C. Allowed to separate @ 80° C. The ester thus separated was then treated with 25 gms. water, and 1 gm. sodium chloride. The top layer was collected and further treated with 25 gm. water and 1 gm. sodium chloride. Allowed to stand and then separated the ester layer which was nearly water-white liquid yet hazy due to some moisture held by the compound. Product of the reaction was vacuum dried @ 10-15 mm. Hg. and 110°-120° C. over 45 minutes and then treated with 0.5% Magnesol and 0.25% Celatom FW-60 and subsequently filtered. The product collected was a clear water-white liquid and weighed 170 gms.

EXAMPLE 10

Foam Tests

Model shampoo formulations comprised of benzoate ester, surfactant, an alkanolamide and water, at concentrations indicated, were investigated for foam properties and characteristics utilizing the technique known as 'Ross-Miles' foaming test. This test procedure, performed at 40±2° C., under the indicated conditions, is a relatively standard foam test in and is readily accepted by the cosmetics and toiletries industries.

Table I shows that the benzoic acid esters of this invention will increase the foam volumes of synthetic detergents (A-E), soaps (F-I) and soap syndets (J-L)

whereas the corresponding alcohol reactant decreases foam volumes.

TABLE I
ROSS-MILES FOAM TEST
Test Conditions: Temperature 40 ± 2° C.; Water Harness 0°H; Test Concentration 0.12% wt/wt.

| COMPONENT | (%) | | | | | (%) | | | | (%) | | |
|---|---|---|---|---|---|---|---|---|---|---|---|---|
|  | A** | B | C | D | E | F** | G | H | I | J** | K | L |
| Sodium Laureth (3) Sulfate | 12.0 | 12.0 | 12.0 | 12.0 | 12.0 | — | — | — | — | — | — | — |
| Sodium (Tallow) Soap | — | — | — | — | — | 12.0 | 12.0 | 12.0 | 12.0 | — | — | — |
| Sodium Cocoyl Isethionate/ Sodium (Tallow) Soap, 1:5 | — | — | — | — | — | — | — | — | — | 12.0 | 12.0 | 12.0 |
| Lauramide DEA | 3.0 | 3.0 | 3.0 | 3.0 | 3.0 | — | — | — | — | — | — | — |
| Octyldodecyl Benzoate (Invention) | — | — | 5.0 | — | — | — | 2.5 | — | 5.0 | — | 5.0 | 2.5 |
| Stearoxy PPG-15 Benzoate (Invention) | — | — | — | — | 2.5 | — | — | 5.0 | — | — | — | — |
| Octyldodecanol | — | 5.0 | — | — | — | — | — | — | — | — | — | — |
| PPG-15 Stearyl Ether | — | — | — | 5.0 | — | — | — | — | — | — | — | — |
| Water | 85.0 | 80.0 | 80.0 | 80.0 | 82.5 | 88.0 | 85.5 | 83.0 | 83.0 | 88.0 | 83.0 | 85.5 |
| pH | 6.5 | 6.4 | 6.4 | 6.2 | 6.6 | 9.8 | 10.0 | 9.8 | 9.7 | 9.7 | 9.4 | 9.7 |
| Results* | 155/150 | 145/140 | 165/155 | 125/110 | 160/150 | 150/150 | 170/170 | 160/158 | 175/175 | 155/155 | 165/165 | 170/167 |

*represented as mm foam @ t = 0/mm foam @ t = 5 min
**Controls
% by weight

EXAMPLE 11

Use of compounds in cosmetic and toiletry compositions, particularly aqueous surfactant compositions

| Soap Based Shampoo | % wt/wt | Synthetic Detergent Based Shampoo | % wt/wt |
|---|---|---|---|
| "Neat Soap"* | 20.0 | Sodium Laureth Sulfate | 12.0 |
| Sodium Cocoyl Isethionate | 2.0 | Lauramide DEA | 3.0 |
|  |  | Stearoxy-PPG-15 Benzoate | 2.5 |
| Octyldodecyl Benzoate | 2.5 |  |  |
| Water | 75.5 | Water | 82.5 |
| Color | q.s. | Color | q.s. |
| Fragrance | q.s. | Fragrance | q.s. |

*approximately 30% water.

Each shampoo produces greater foam volume than similar shampoos not having the benzoic acid esters.

What is claimed is:

1. A method of modifying while not suppressing foam in an aqueous surfactant composition comprising admixing with the aqueous composition a foam modifying amount of a substantially pure benzoate ester composition of the formula:

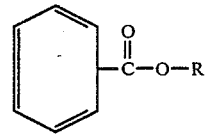

wherein R is

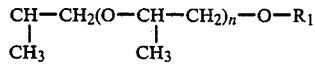

wherein n is 9–16 and $R_1$ is a branched or linear alkyl of 3 to 22 carbon atoms.
whereby the foam is modified but not suppressed.

2. The method of claim 1, wherein n is 14.
3. The method of claim 2, wherein $R_1$ is $C_{18}H_{37}$.
4. The method of claim 2, wherein $R_1$ is $C_4H_9$.
5. A benzoate ester of the formula:

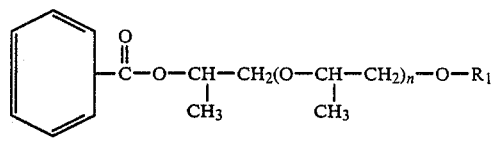

wherein n is 9 to 16 and $R_1$ is a branched or linear alkyl of 3 to 22 carbon atoms.

6. The ester of claim 5, wherein n is 14.
7. The ester of claim 6, wherein $R_1$ is $C_{18}H_{37}$.
8. The ester of claim 6, wherein $R_1$ is $C_4H_9$.
9. The ester of claim 5, wherein $R_1$ is $C_{16}H_{33}$.
10. The ester of claim 9, wherein n is 9.

* * * * *